(12) United States Patent
Love et al.

(10) Patent No.: US 9,724,256 B2
(45) Date of Patent: *Aug. 8, 2017

(54) DISPOSABLE ABSORBENT LIFT DEVICE

(71) Applicant: Medline Industries, Inc., Mundelein, IL (US)

(72) Inventors: Dan Love, Libertyville, IL (US); Scott A. Smith, Mundelein, IL (US); Steve A. Maskrey, Crystal Lake, IL (US); Paul I. Bottcher, Lakemoor, IL (US)

(73) Assignee: Medline Industries, Inc., Mundelein, IL (US)

( * ) Notice: Subject to any disclaimer, the term of this patent is extended or adjusted under 35 U.S.C. 154(b) by 426 days.

This patent is subject to a terminal disclaimer.

(21) Appl. No.: 13/712,171

(22) Filed: Dec. 12, 2012

(65) Prior Publication Data

US 2014/0207096 A1    Jul. 24, 2014

Related U.S. Application Data

(63) Continuation of application No. 12/869,432, filed on Aug. 26, 2010, now Pat. No. 8,791,321.

(51) Int. Cl.
*A61F 13/51* (2006.01)
*A61G 7/057* (2006.01)
(Continued)

(52) U.S. Cl.
CPC .............. *A61G 7/057* (2013.01); *A61F 5/48* (2013.01); *A61F 13/513* (2013.01);
(Continued)

(58) Field of Classification Search
CPC ...... A61G 1/01; A61G 2200/32; A61G 7/103; A61F 13/51478; B32B 2307/73; B32B 2307/724
(Continued)

(56) References Cited

U.S. PATENT DOCUMENTS 1,334,901 A    3/1920    Higdon
3,414,459 A    12/1968   Wells
(Continued)

FOREIGN PATENT DOCUMENTS

CN    2155842    2/1994
EP    0642614 A1    3/1995
(Continued)

OTHER PUBLICATIONS

"Adhesive", Wikipedia, 13 pages, accessed on Jun. 10, 2015 at: http://en.wikipedia.org/wiki/Adhesive.
(Continued)

*Primary Examiner* — Peter S Vasat
(74) *Attorney, Agent, or Firm* — Cooley LLP (57) ABSTRACT

The present invention relates to a disposable absorbent pad comprising multiple layers. In particular, the absorbent pad of the present invention maintains skin dryness by absorbing moisture while preventing leakage to the skin or the bed linens, allowing air circulation at the surface of the patient's skin to prevent heat buildup, and is strong enough to allow the patient to be repositioned, even when the pad is wet. In a particular embodiment the first layer is comprised of a fluid-permeable, porous material, the second layer is disposed under the first layer and is comprised of at least one super absorbent material, and a base layer disposed under the second layer.

39 Claims, 2 Drawing Sheets

(51) Int. Cl.

| | | |
|---|---|---|
| *A61F 5/48* | (2006.01) | |
| *A61F 13/514* | (2006.01) | |
| *A61F 13/53* | (2006.01) | |
| *B32B 5/02* | (2006.01) | |
| *B32B 5/08* | (2006.01) | |
| *B32B 5/26* | (2006.01) | |
| *B32B 7/14* | (2006.01) | |
| *B32B 27/12* | (2006.01) | |
| *B32B 27/32* | (2006.01) | |
| *A61F 13/513* | (2006.01) | |
| *A61F 13/539* | (2006.01) | |
| *A61L 15/24* | (2006.01) | |
| *A61L 15/28* | (2006.01) | |
| *A61F 13/15* | (2006.01) | |
| *A61G 7/10* | (2006.01) | |

(52) U.S. Cl.
CPC .. *A61F 13/51462* (2013.01); *A61F 13/51478* (2013.01); *A61F 13/53* (2013.01); *A61F 13/539* (2013.01); *A61L 15/24* (2013.01); *A61L 15/28* (2013.01); *B32B 5/022* (2013.01); *B32B 5/08* (2013.01); *B32B 5/26* (2013.01); *B32B 7/14* (2013.01); *B32B 27/12* (2013.01); *B32B 27/32* (2013.01); *A61F 2013/15024* (2013.01); *A61F 2013/15056* (2013.01); *A61F 2013/15154* (2013.01); *A61G 7/05715* (2013.01); *A61G 7/1026* (2013.01); *A61G 2007/05784* (2013.01); *B32B 2262/02* (2013.01); *B32B 2262/067* (2013.01); *B32B 2262/14* (2013.01); *B32B 2307/54* (2013.01); *B32B 2307/718* (2013.01); *B32B 2307/7163* (2013.01); *B32B 2307/724* (2013.01); *B32B 2307/726* (2013.01); *B32B 2307/728* (2013.01); *B32B 2307/73* (2013.01)

(58) Field of Classification Search
USPC ...... 442/76, 118; 5/81.1 R, 81.1 T, 501, 484, 5/626; 428/91; 604/378, 385.23
See application file for complete search history.

(56) References Cited

U.S. PATENT DOCUMENTS

| | | | |
|---|---|---|---|
| 3,547,723 A | 12/1970 | Gresham et al. | |
| 3,556,907 A | 1/1971 | Nystrand et al. | |
| 3,575,349 A | 4/1971 | Fend et al. | |
| 3,691,570 A | 9/1972 | Gaines et al. | |
| 3,692,622 A | 9/1972 | Dunning et al. | |
| 3,779,246 A | 12/1973 | Mesek et al. | |
| 3,829,914 A | 8/1974 | Treat | |
| 3,849,813 A | 11/1974 | Neilson | |
| 3,867,872 A | 2/1975 | Nystrand | |
| 3,886,941 A | 6/1975 | Duane et al. | |
| 3,949,035 A | 4/1976 | Dunning et al. | |
| 3,954,554 A | 5/1976 | Curry et al. | |
| 4,011,034 A | 3/1977 | Curry et al. | |
| 4,046,622 A | 9/1977 | Attwood et al. | |
| 4,077,410 A | 3/1978 | Butterworth et al. | |
| 4,111,744 A | 9/1978 | Reiniger | |
| 4,154,883 A | 5/1979 | Elias | |
| 4,160,004 A | 7/1979 | Curry et al. | |
| 4,320,162 A | 3/1982 | Schulz | |
| 4,360,015 A | 11/1982 | Mayer | |
| 4,476,078 A | 10/1984 | Tao | |
| 4,533,507 A | 8/1985 | Tao | |
| 4,572,440 A | 2/1986 | Tao | |
| 4,639,254 A | 1/1987 | Legault et al. | |
| 4,675,925 A | 6/1987 | Littleton | |
| D301,088 S | 5/1989 | Kawaguchi | |
| 4,937,115 A | 6/1990 | Leatherman | |
| 5,128,193 A | 7/1992 | Anapol et al. | |
| 5,135,792 A | 8/1992 | Hogan | |
| 5,141,794 A * | 8/1992 | Arroyo | 428/138 |
| 5,173,351 A | 12/1992 | Ruppel et al. | |
| 5,249,320 A | 10/1993 | Moretz et al. | |
| 5,329,655 A | 7/1994 | Garner | |
| 5,422,172 A | 6/1995 | Wu | |
| 5,500,063 A | 3/1996 | Jessup | |
| 5,555,801 A | 9/1996 | Kroyer | |
| 5,701,617 A | 12/1997 | Colby | |
| 5,733,628 A | 3/1998 | Pelkie | |
| 5,735,145 A | 4/1998 | Pernick | |
| 5,743,999 A | 4/1998 | Kamps et al. | |
| 5,787,523 A | 8/1998 | Lindberg | |
| 5,833,678 A | 11/1998 | Ashton et al. | |
| 5,837,627 A | 11/1998 | Halabisky et al. | |
| 5,843,056 A | 12/1998 | Good et al. | |
| 5,996,148 A | 12/1999 | McCain et al. | |
| 6,063,981 A | 5/2000 | Wehner et al. | |
| 6,118,218 A | 9/2000 | Yializis et al. | |
| 6,245,414 B1 | 6/2001 | Biagiotti | |
| 6,274,520 B1 | 8/2001 | Cordell | |
| 6,420,625 B1 | 7/2002 | Jones et al. | |
| 6,560,793 B2 | 5/2003 | Walker | |
| 6,658,676 B1 | 12/2003 | Persson et al. | |
| 6,675,702 B1 | 1/2004 | Maksimow | |
| 6,818,083 B2 | 11/2004 | Mcamish et al. | |
| 6,874,176 B2 | 4/2005 | Berge | |
| 7,240,384 B2 | 7/2007 | DuDonis | |
| 7,361,803 B2 | 4/2008 | Miskie | |
| 7,521,587 B2 | 4/2009 | Busam et al. | |
| 7,531,587 B2 | 5/2009 | Norris | |
| 7,818,836 B2 | 10/2010 | Stinson | |
| 7,886,411 B2 | 2/2011 | Jezzie et al. | |
| 8,122,570 B2 | 2/2012 | Jezzie | |
| 8,791,321 B2 * | 7/2014 | Love et al. | 604/378 |
| 2003/0082966 A1 | 5/2003 | Menday et al. | |
| 2003/0084983 A1 | 5/2003 | Rangachari et al. | |
| 2003/0148091 A1 | 8/2003 | Ikeda et al. | |
| 2003/0190852 A1 * | 10/2003 | Dutkiewicz et al. | 442/181 |
| 2004/0048542 A1 * | 3/2004 | Thomaschefsky et al. | 442/389 |
| 2005/0148253 A1 * | 7/2005 | Koslow | 442/118 |
| 2006/0060147 A1 | 3/2006 | Appelhans | |
| 2006/0216473 A1 | 9/2006 | Tomany et al. | |
| 2006/0264863 A1 | 11/2006 | Blyth | |
| 2007/0003764 A1 | 1/2007 | Muslet | |
| 2007/0056096 A1 * | 3/2007 | Assink | 5/81.1 HS |
| 2008/0174128 A1 | 7/2008 | Jezzi | |
| 2009/0004452 A1 | 1/2009 | Assink | |
| 2009/0075346 A1 | 3/2009 | Chen et al. | |
| 2011/0190720 A1 | 8/2011 | Skroesen | |
| 2012/0053545 A1 | 3/2012 | Love et al. | |
| 2013/0198955 A1 | 8/2013 | Lishnevsky et al. | |
| 2014/0352071 A1 | 12/2014 | Love et al. | |

FOREIGN PATENT DOCUMENTS

| | | |
|---|---|---|
| EP | 1291380 A1 | 3/2003 |
| WO | WO 93/04113 A1 | 3/1993 |
| WO | WO 94/23128 A1 | 10/1994 |
| WO | WO 95/25495 A1 | 9/1995 |
| WO | WO 00/16913 A1 | 3/2000 |
| WO | WO 00/16914 A1 | 3/2000 |
| WO | WO 01/92386 A1 | 12/2001 |

OTHER PUBLICATIONS

"Hot-melt adhesive", Wikipedia, 5 pages, accessed on Jun. 10, 2015 at: http://en.wikipedia.org/wiki/Hot-melt_adhesive.
"Spunbond Technology", 6 pages, accessed on Jun. 10, 2015 at: http://www.engr.utk.edu/mse/Textiles/Spunbond%20Technology.htm.
"Standard Test Method for Tensile Properties of Thin Plastic Sheeting", Designation: D882-09, ASTM International (2009), pp. 1-9.
"Superabsorbent polymer", Wikipedia, 5 pages, accessed on Jun. 10, 2015 at: http://en.wikipedia.org/wiki/Superabsorbent_polymer.
Tyvek Styles Chart, 1 page, accessed on Feb. 17, 2015 at: http://www2.dupontcom/Tyveklen_US/assels/images/tyvek_styles_chart.jpg.

(56) References Cited

OTHER PUBLICATIONS

European Application No. EP 11179071.3, European Search Report, mailed Mar. 28, 2012, 5 pages.
European Application No. EP 14168533.9, European Search Report, mailed Sep. 5, 2014, 3 pages.
European Application No. EP 11179071.3, Notice of Opposition by Mr. Paul Openshaw, dated Mar. 3, 2015, 36 pages.
International Search Report in International Application No. PCT/US2014/27095, dated Jul. 7, 2014, 3 pages.
"87240 Tyvek.RTM. 1622 E", accessed at: http://kremerpigments.com/shopus/PublishedFiles/87240e.pdf on Apr. 10, 2013.
Dupont Technical Reference Guide, accessed at: http://www2.dupont.com/Medical.sub.--Packaging/en.sub.--US/assets/downloads/DMP11.sub.--17282.sub.--Tech.sub.--Reference.sub.--Guide.sub.--me03.pdf on Apr. 10, 2013.
"Air-Permeable Premium Drypad. Allows Air to Flow Through- and nothing else!", Ultrasorbs AP Brochure LIT152R, Medline Industries, Inc. (2008), 4 pages.
"Etac 4Way LPL Bed Management System", Etac AB Catalog, IM85/200LPL, IM85/200LPLNS, IM85/2003LPLNS, Etac AB (2009), 2 pages.
"Ultrasorbs® AP Premium DryPads. Air-Permeable Drypads Allow Air to Flow Through- and nothing else!", Ultrasorbs Catalog LIT050, Medline Industries, Inc., Mar. 12, 2009, pp. 10-11.
"Ultrasorbs® AP Premium DryPads. We Believe in Skin Dryness. Pressure Ulcers: An Industry-Wide Concern", Ultrasorbs Brochure LIT735, Medline Industries, Inc. (2009), 4 pages.
"Wings Quilted Cloth-like Underpads!", Announcement to Customers, Covidien, Feb. 2010, 2 pages.
"Wings Quilted Premium Underpads", Covidien (Mar. 2009), 4 pages.
PCT/US2014/27095, Written Opinion dated Jul. 7, 2014, 8 pages.
Preliminary Opinion for European Patent Application No. 11179071.3, dated Jul. 27, 2016, 9 pages.

\* cited by examiner

DISPOSABLE ABSORBENT LIFT DEVICE

CROSS REFERENCE TO OTHER APPLICATIONS

This application is a continuation of U.S. patent application Ser. No. 12/869,432, filed Aug. 26, 2010, which is incorporated by reference herein in its entirety.

BACKGROUND

Bed sores, also known as pressure ulcers or decubitus ulcers, are prevalent among people who are bed-ridden or otherwise immobilized. Skin ulcers can be caused by pressure exerted on the skin and soft tissues (e.g., the individual's body weight resting against a hard surface such as a bed or chair) and are exacerbated when the skin is also exposed to moisture (e.g., due to incontinence) and/or friction, heat, and shear forces, for example caused by moving or repositioning a bed-ridden patient.

Elderly nursing home residents are particularly vulnerable to pressure ulcers since they are frequently bed-ridden and incontinent. Approximately one out of ten nursing home residents have some form of pressure ulcers. Since pressure ulcers can be persistent and heal slowly, treating pressure ulcers once formed is thus expensive, so there is a significant need to minimize a patient's exposure to conditions which would cause such ulcers.

For example, it would be beneficial for bed-ridden persons who are incontinent or have other moisture management issues to lay on a pad or layer which would not only absorb moisture but also maintain skin dryness. It would also be useful to protect the bed and linens from moisture as well in order to maintain hygiene and minimize the need for hospital staff to change bed linens. Additionally, in order to minimize heat build up between the bedding and the patient's skin, and to maintain skin health, it would be beneficial for the absorbent pad or layer to allow air circulation between the pad and the skin. Furthermore, since bed-ridden patients need to be lifted and repositioned, for example to change bed linens, for medical procedures, or to prevent the formation of pressure ulcers, it would be useful for the absorbent pad to have sufficient strength to allow such repositioning.

Current products do not provide a solution to all four needs: 1) maintaining skin dryness 2) protecting the bed and linens, 3) allowing air circulation, and 4) allowing caregivers to reposition the individual. Typically a caregiver will combine up to eight disposable underpads to absorb moisture, as well as reusable cloth underpads or sheets to protect the bed and linens and to lift and reposition the patient.

Combinations of multiple absorbent products are less than ideal for several reasons. From a strictly practical standpoint, using multiple absorbent products is more expensive, and requires more packaging, storage, shipping costs, waste, and the like. Reusable cloth underpads, or drawsheets, are also the second most expensive item for hospitals to launder and process. Moreover, the combination of multiple products is not very effective in preventing damage to the skin, while at the same time protecting bedding. Multiple layers of absorbent pads can increase the shear and friction experienced by individuals as the layers slide and shift against each other. Furthermore, conventional disposable pads disintegrate when wet, and reusable cloth underpads prevent air circulation. Furthermore, the thickness of the multiple layers can interfere with 'pressure management' beds and surfaces which distribute weight to minimize or prevent excessive pressure.

There is therefore a need for an absorbent pad which maintains skin dryness by absorbing moisture while preventing leakage to the skin or the bed linens, allowing air circulation at the surface of the patient's skin to prevent heat buildup, and which is strong enough to allow the patient to be repositioned, even when the pad is wet.

DETAILED DESCRIPTION OF THE INVENTION

In various embodiments, the present invention is directed towards an absorbent pad comprising multiple layers, e.g., three or more layers, wherein the first layer is comprised of a fluid-permeable, porous material, the second layer is disposed under the first layer and is comprised of at least one super absorbent material, and a base layer disposed under the second layer. Additionally, the base layer has a tensile strength at break, when measured by the ASTM D 882 method, in the range of about 45 N/25 mm to 100 N/25 mm in the machine direction and about 30 to 60 N/25 mm in the cross direction.

In certain embodiments of the invention, the base later is comprised of a third layer comprised of a hydrophobic, breathable film, disposed under the second layer and a fourth layer, disposed under the third layer, comprised of an air-permeable material.

In one embodiment of the invention, the first layer is a nonwoven material. The nonwoven material of the first layer can be manufactured using any technique known in the art. Non-limiting examples of suitable types of nonwoven materials include staple nonwoven materials, melt-blown nonwoven materials, spunmelt nonwoven materials, spunbond nonwoven materials, SMS (spunbond meltblown spunbond) materials, spun lace materials, needle-felted materials, thermal-bonded nonwoven materials, trough-air-bonded nonwoven material, spunlaid nonwoven material, air-laid nonwoven materials or the like, or any combinations thereof.

In certain embodiments of the invention the first layer is hydrophilic. For example, the first layer can be treated in order make it fluid permeable. Such treatments can include any treatment known in the art which renders a material fluid permeable. Non-limiting examples of such treatments include: coating the surface of the material with a hydrophilic surfactant as described in WO 93/04113 entitled "Method for hydrophilizing absorbent foam materials" and in WO 95/25495 entitled "Fluid acquisition and distribution member for absorbent core"; surface treatments such as corona and plasma treatment as described in described in U.S. Pat. No. 6,118,218 entitled "Steady-state glow-discharge plasma at atmospheric pressure"; applying a hydrophilic coating by a plasma polymerization process as described in WO 00/16913 entitled "Durably wettable, liquid pervious webs" and WO 00/16914 entitled "Durably wettable, liquid pervious webs prepared using a remote plasma polymerization process"; or contacting the fibers with a solution of hydrophilic monomers and radical polymerization initiators and exposing the fibers to UV radiation as described in U.S. Pat. No. 7,521,587 entitled "Absorbent articles comprising hydrophilic nonwoven fabrics"; all of which are hereby incorporated by reference in their entirety for all purposes.

In another embodiment of the invention, the first layer is permeable to fluids such that the fluids can pass through the surface of the first layer toward the second layer (disposed beneath the first layer), but the fluids cannot substantially reverse direction and move back toward the surface of the first layer. In other words, in various embodiments the flow of fluids through the first layer is substantially unidirectional from the top surface of the first layer toward the second layer disposed beneath the first layer.

The first layer can comprise any suitable material known in the art. For example, the first layer can comprise a polymeric material. Non limiting examples of such polymeric materials include polypropylene, polyethylene, polyethylene terephthalate, polyamide, viscose rayon, nylon, or the like or any combinations thereof. Furthermore, the polymeric material can be a biodegradable polymeric material. One such non-limiting example of a polymer is the starch-based biodegradable material described in United States Patent Application 2009/0075346, which is hereby incorporated by reference for all purposes. In certain embodiments of the invention, the first layer has a weight per unit area (weight) in the range of about 15 gsm (grams per square meter) to about 20 gsm. For example, the first layer can have a weight of about 15 gsm, about 16 gsm, about 17 gsm, about 18 gsm, about 19 gsm, or about 20 gsm, inclusive of all ranges and subranges therebetween.

In certain embodiments of the invention, the first layer is fluid permeable. In one embodiment of the invention the first layer has a Moisture Transfer Rate, for example as measured by ASTM E96M-05 in the range of about 5 to about 200 sec/mL.

In another embodiment of the invention, the first layer is air permeable. In certain embodiments, the first layer has an air permeability of the range of about 10 seconds/100 mL to about 100 seconds/100 mL, including about 10 seconds/100 mL, about 20 seconds/100 mL, about 30 seconds/100 mL, about 40 seconds/100 mL, about 50 seconds/100 mL, about 60 seconds/100 mL, about 70 seconds/100 mL, about 80 seconds/100 mL, about 90 seconds/100 mL, or about 100 seconds/100 mL, inclusive of all ranges and subranges therebetween, for example as measured by the Gurely method using a densometer, (e.g., methods conforming the following standards: ASTM D737 and WSP 70.1).

The second layer of the absorbent pad of the present invention is disposed beneath the first layer, as described herein. For example, the second layer can be located directly beneath the first layer and in direct contact with the first layer, or adhered to the first layer by means of one or more intervening layers, for example an adhesive layer and/or a spacer layer.

In certain embodiments the second layer is comprised of a formed material. The formed material of the second layer can be manufactured using any technique known in the art. Non-limiting examples of suitable types of formed materials include staple nonwoven materials, melt-blown nonwoven materials, spun-melt nonwoven materials, spun-bound nonwoven materials, thermal-bonded nonwoven materials, trough-air-bonded nonwoven materials, spun-laid nonwoven materials, air-laid nonwoven materials, or any combinations thereof. In a particular embodiment the second layer is comprised of an air-laid fiber. In one embodiment the air-laid fiber is thermobonded. In a particular embodiment the air-laid material is air laid paper.

The second layer can comprise fibers, for example natural fibers. The natural fibers can be any suitable natural fibers known in the art. In one embodiment the natural fiber is cellulose. The cellulose can be from any suitable source known in the art. Non-limiting examples of suitable sources of cellulose are wood fibers, plant fibers, field crop fibers, fluff pulp fibers, cotton, any other material, man-made or natural, designed to absorb fluid, or any combination thereof. In a particular embodiment the second layer comprises wood fibers. In another embodiment, the second layer comprises macerated wood pulp.

The second layer of the pad can further comprise an absorbent polymer, for example any super-absorbent polymer known in the art. Non-limiting examples of suitable super-absorbent polymers include, for example, polymers and copolymers of acrylic acid and salts thereof (including alkali metal salts such as sodium salts, or alkaline earth salts thereof), polymers and copolymers of methacrylic acid and salts thereof (including alkali metal salts such as sodium salts, or alkaline earth salts thereof), polyacrylamide polymers and copolymers, ethylene maleic anhydride copolymers, cross-linked carboxy-methyl-celluloses, polyacrylate/polyacrylamide copolymers, polyvinyl alcohol copolymers, cross-linked polyethylene oxides, starch grafted copolymers of polyacrylonitrile, etc. The super-absorbent polymers can be cross-linked to suitable degree.

In a particular embodiment the super-absorbent polymer comprises sodium polyacrylate. In another embodiment, the second layer comprises an amount of super-absorbent polymer(s) in the range of about 15 gsm to about 35 gsm. For example, the super-absorbent polymer(s) in the second layer is present in an amount of about 15 gsm, about 20 gsm, about 25 gsm, about 30 gsm, or about 35 gsm, inclusive of all ranges and subranges therebetween.

In another embodiment, the cellulose fibers of the second layer are present in the second layer in an amount of about 85 gsm to about 115 gsm. For example, the cellulose fibers of the second layer are present in an amount of about 85 gsm, about 90 gsm, about 95 gsm, about 100 gsm, about 103 gsm, about 105 gsm, about 110 gsm, about 115 gsm, or about 120 gsm, inclusive of all ranges and subranges therebetween.

In a particular embodiment, the second layer is a thermobonded, absorbent airlaid core made from cellulose fibers and super-absorbent polymers. In a particular embodiment of the invention, the second layer is comprised of an airlaid absorbent core as described in U.S. Pat. No. 6,675,702 which is hereby incorporated herein by reference for all purposes. In yet another embodiment, the second layer is comprised of a thermobonded airlaid core made from about 100 to about 105 gsm of cellulose fibers and 25 gsm of super absorbent polymers. In a particular embodiment, the cellulose fibers are macerated wood pulp.

The second layer absorbs substantially all of the fluids penetrating through from the first layer, and has a fluid-holding capacity sufficient to retain fluids without releasing the fluid through the first layer or through the third and fourth layers. In certain embodiments, the second layer has an absorption capacity in the range of about 50 $cc/m^2$ to about 20,000 $cc/m^2$, for example, about 50 $cc/m^2$, about 100 $cc/m^2$, about 150 $cc/m^2$, about 200 $cc/m^2$, about 250 $cc/m^2$, about 300 $cc/m^2$, about 350 $cc/m^2$, about 400 $cc/m^2$, about 450 $cc/m^2$, about 500 $cc/m^2$, about 550 $cc/m^2$, about 600 $cc/m^2$, about 650 $cc/m^2$, about 700 $cc/m^2$, about 750 $cc/m^2$, about 800 $cc/m^2$, about 850 $cc/m^2$, about 900 $cc/m^2$, about 1,000 $cc/m^2$, about 1,100 $cc/m^2$, about 1,200 $cc/m^2$, about 1,300 $cc/m^2$, about 1,400 $cc/m^2$, about 1,500 $cc/m^2$, about 1,600 cc/m², about 1,700 cc/m², about 1,800 cc/m², about 1,900 cc/m², about 2,000 cc/m², about 3,000 cc/m², about 4,000 cc/m², about 5,000 cc/m², about 6,000 cc/m², about 7,000 cc/m², about 8,000 cc/m², about 9,000 cc/m², about 10,000 cc/m², about 11,000 cc/m², about 12,000 cc/m², about 13,000 cc/m², about 14,000 cc/m², about, 15,000 cc/m², about 16,000 cc/m², about 17,000 cc/m², about, 18,000 cc/m², about 19,000 cc/m², or about 20,000 cc/m² inclusive all ranges and subranges therebetween, as measured by the ISO11948-1 test method.

In a particular embodiment of the present invention, the second layer can be comprised of more than one fluid absorbing layer (also known as "core" layers). For example, the second layer can comprise two (or more) layers, each comprising the same or different absorbent polymer.

In order to minimize or prevent the formation of ulcers in a patient using the absorbent pad of the present invention, the pad should remain as uniform in thickness as possible, even after absorbing fluids from the patient. Accordingly, the pad should not swell substantially, nor should the various layers in contact with the absorbent (second) layer separate within the pad. Applicants have found that air laid materials comprising a combination of a cellulosic material and a superabsorbent polymer, as described herein do not substantially swell or separate from the other layers (e.g., the first and/or third layers) when wetted with fluids from the patient. By "not swell substantially" we mean that the absorbent second layer does not increase in thickness more than about 200%, for example less than about 200%, less than about 190%, less than about 180%, less than about 170%, less than about 160%, less than about 150%, less than about 140%, less than about 130%, less than about 120%, less than about 110%, less than about 100%, less than about 90%, less than about 80%, less than about 70%, less than about 60%, less than about 50%, less than about 40%, less than about 30%, less than about 20%, or less than about 10% in thickness, inclusive of all ranges and subranges therebetween. By "not substantially separate", we mean that at least about 60%, for example less than about 60%, less than about 50%, less than about 40%, less than about 30%, less than about 20%, or less than about 10%, of the surface area of the absorbent second layer remains adhered to or in direct contact with the first and third layers of the absorbent pad (or remains adhered to or in direct contact with an adhesive and/or spacer layer disposed between the first and/or third layers and the absorbent second layer).

The base layer prevents fluid absorbed in the second layer from going through the bottom of the absorbent pad. The base layer should also provide for air circulation within the absorbent pad to prevent heat and moisture vapor build up.

In certain embodiments of the invention, the base layer is comprised of a third and fourth layer, wherein the third layer is disposed under the second layer and the fourth layer disposed under the third layer.

The base layer (or in certain embodiments, the third layer) prevents the fluid absorbed in the second layer to penetrate through the base layer of the absorbent pad (or in some embodiments, the fourth layer). The base layer can comprise any natural or man-made material capable of preventing the flow of fluids out of the second layer and through the bottom of the absorbent pad. In certain embodiments wherein the base layer comprises a third and fourth layer, the third layer comprises a polymeric film, for example a hydrophobic polymeric film. The polymeric film of the third layer can be any suitable polymer known in the art, for example suitable hydrophobic polymers. Non-limiting examples of such polymers include polyolefins such as polyethylene, polypropylene, poly(lactic acid), polyhydroxybutyrate, and tapioca starch as well as copolymers thereof. One such non-limiting example of a polymer is the starch-based biodegradable material described in United States Patent Application 2009/0075346, which is hereby incorporated herein by reference for all purposes.

The base layer should also provide for air circulation within the absorbent pad to prevent heat and moisture vapor build up. Accordingly, in particular embodiments, the base layer is air permeable. Air permeability can be provided in various ways, for example by forming a base layer comprising a third and fourth, wherein the third layer comprises a woven or nonwoven hydrophobic material which prevents the movement of bulk fluid, but allows diffusion or movement of air through the third layer. For example, the hydrophobic material can comprise hydrophobic polymeric fibers (e.g., polyolefin fibers) or comprising fibers surface treated with a hydrophobic sizing or coating. In yet another embodiment the third layer comprises a perforated polyolefin (e.g. polyethylene and/or polypropylene polymer or copolymer) sheet. If the third layer comprises a perforated polyolefin sheet, the perforations should be of a size which does not permit the permeation or movement of liquids through the perforations, but does provide air permeability values within the ranges described herein.

Although the base layer does not permit any appreciable amount of liquid to flow through, in many instances it can be advantageous to allow moisture vapor to permeate through the base layer. In certain embodiments of the invention, for a base layer comprising a third and fourth layer, the third layer has a moisture vapor transmission rate (MTVR) in the range of about 1,000 g/m²/day to about 10,000 g/m²/day. For example, the third layer can have an MTVR of about 1,000 g/m²/day, about 2,000 g/m²/day, about 3,000 g/m²/day, about 4,000 g/m²/day, about 5,000 g/m²/day, about 6,000 g/m²/day, about 7,000 g/m²/day, about 8,000 g/m²/day, about 9,000 g/m²/day, or about 10,000 g/m²/day, inclusive of all ranges and subranges therebetween.

In yet another embodiment of the invention, the third layer has a moisture vapor transmission rate (MTVR) in the range of about 2,500 g/m²/day to about 4,500 g/m²/day. For example, the third layer can have an MTVR of about 2,500 g/m²/day, about 2,600 g/m²/day, about 2,700 g/m²/day, about 2,800 g/m²/day, about 2,900 g/m²/day, about 3,000 g/m²/day, about 3,100 g/m²/day, about 3,200 g/m²/day, about 3,300 g/m²/day, about 3,400 g/m²/day, about 3,500 g/m²/day, about 3,600 g/m²/day, about 3,700 g/m²/day, about 3,800 g/m²/day, about 3,900 g/m²/day, about 4,000 g/m²/day, about 4,100 g/m²/day, about 4,200 g/m²/day, about 4,300 g/m²/day, about 4,400 g/m²/day or about 4,500 g/m²/day, inclusive of all ranges and subranges therebetween.

In various embodiments of the present invention wherein the base layer comprises a third and fourth layer, the third layer has a weight in the range of about 20 gsm to about 45 gsm. For example, the third layer can have a weight of about 20 gsm, 25 gsm, 30 gsm, 35 gsm, 40 gsm, or 45 gsm inclusive of all ranges and subranges therebetween.

In one embodiment of the invention, the fourth layer is a non-woven material. The non-woven material of the fourth layer can be manufactured using any technique known in the art. Non-limiting examples of suitable types of nonwoven materials include staple nonwoven materials, melt-blown nonwoven materials, spunmelt nonwoven materials, spunbond nonwoven materials, SMS (spunbond meltblown spunbond) materials, spun lace materials, needle-felted materials, thermal-bonded nonwoven materials, trough-air-bonded nonwoven material, spunlaid nonwoven material, air-laid nonwoven materials or the like, or any combinations thereof.

In certain embodiments of the invention the fourth layer is hydrophobic. The fourth layer can be made of any suitable material known in the art. Non limiting examples of such materials include polypropylene, polyethylene, polyethylene terephthalate, polyamide, viscose rayon, nylon, or any combinations thereof or the like. Furthermore, the polymeric material can be a biodegradable polymeric material. One such non-limiting example of a polymer is the starch-based biodegradable material described in United States Patent Application 2009/0075346, which is hereby incorporated herein by reference for all purposes. In certain embodiments of the invention, the fourth layer has a weight in the range of about 30 to about 80 gsm. For example, the fourth layer can have a weight of about 30 gsm, about 35 gsm, about 40 gsm, about 45 gsm, about 50 gsm, about 55 gsm, about 60 gsm, about 65 gsm, about 70 gsm, about 75 gsm, about 80 gsm, about 90 gsm and all sub-ranges between.

Any embodiments of the first layer described herein can be independently combined with any particular embodiments of the second, third, and fourth layers described herein. For example, in a particular embodiment the first layer is a spunbond, nonwoven sheet; the second layer comprises cellulose fibers and super absorbent polymers; the third layer is a perforated polyethylene film and the fourth layer is a nonwoven sheet.

In a certain embodiments, the first layer is a spunbond, nonwoven sheet with a weight of about 10-20 grams; the second layer comprises cellulose fibers and super absorbent polymers; the third layer is a perforated polyethylene film with a weight of about 30 grams and the fourth layer is a nonwoven sheet with a weight of about 40 to 60 gsm.

Figure 1:
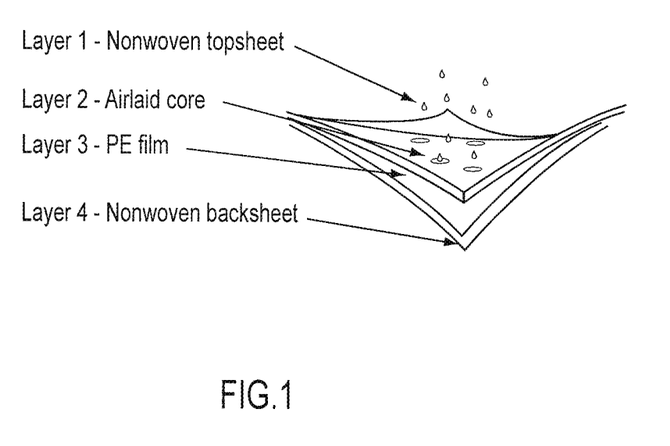
FIG. 1. Cross-section of an embodiment of the absorbent pad of the present invention.

In other embodiments, the first layer is a hydrophilic. SMS polyethylene nonwoven sheet with a weight of about 10 to about 20 gsm; the second layer is a thermobonded absorbent airlaid core comprising about 103 gsm wood pulp fibers and about 25 gsm super absorbent polymers; the third layer is a perforated polyethylene film with a weight of about 20 gsm, and the fourth layer is a nonwoven, BTBS film with a weight of about 50 gsm. See FIG. 1.

In yet other embodiments, the absorbent pad has handles. In a particular embodiment, the handles are formed by extending the dimensions of the base layer beyond the other two layers and forming voids in the backing material. The voids can be formed for fingers or hands. In another embodiment, a suitable material of a suitable size can be adhered to the edge of the absorbent pad to form handles.

In various embodiments, the first, second, and base layers are adhered together. The layers can be adhered together using any suitable technique known in the art. In a particular embodiment, the layers are adhered together using an adhesive. Any suitable adhesive known in the art can be used. The adhesive used can be natural or synthetic. Non-limiting examples of such adhesives are hot melt adhesives, drying adhesives, contact adhesives, UV curing adhesives, light curing adhesives, and pressure sensitive adhesives or the like. In one embodiment, the top layer and the edges where the layers meet are glued together using hot melt adhesive.

In various other embodiments, the pad comprises first, second, third, and fourth layers as described herein, adhered together. The layers can be adhered together using any suitable technique known in the art. In a particular embodiment, the layers are adhered together using an adhesive. Any suitable adhesive known in the art can be used. The adhesive used can be natural or synthetic. Non-limiting examples of such adhesives are hot melt adhesives, drying adhesives, contact adhesives, UV curing adhesives, light curing adhesives, and pressure sensitive adhesives or the like. In one embodiment, the top layer and the edges where the layers meet are glued together using hot melt adhesive.

Non-limiting examples of adhesives include animal glue, collagen-based glue, albumin glue, casein glue, Canada balsam, coccoina, pelikanol, gum Arabic, latex, methyl cellulose, library glue, mucilage, resorcinol resin, starch, urea-formaldehyde resin, acrylonitrile, cyanoacrylate, acrylic, epoxy resins, epoxy putty, ethylene-vinyl acetate, phenol formaldehyde resin, polyamide, polyester resins, polyethylene, polypropylene, polysulfides, polyurethane, polyvinyl acetate, polyvinyl alcohol, polyvinyl chloride, polyvinyl chloride emulsion, polyvinylpyrrolidone, rubber cement, silicones, styrene acrylic copolymer, ethylene-acrylate copolymers, polyolefins, atactic polypropylene, polybutene-1, oxidized polyethylene, styrene block copolymers, polycarbonates, fluoropolymers, silicone rubbers, or the like and various other co-polymers. The adhesive may further comprise one or more additives. Any suitable additive known in the art can be used. Non-limiting examples of additives include, tackifying resins, waxes, plasticizers, anti-oxidants, stabilizers, UV stabilizers, pigments, dyes, biocides, flame retardants, antistatic agents, and fillers or the like. In particular embodiments, the adhesive comprises a hot-melt adhesive.

The adhesive layer(s) can be continuous, contacting substantially the entire surface area of any two layers adhered together (e.g. at least about 75%, at least about 80%, at least about 85%, at least about 90%, at least about 90%, or essentially about 100% of the surface area of the two layers adhered together, inclusive of all ranges and subranges therebetween). That is, the adhesive forms an intermediate layer between any two layers adhered together, contacting substantially the entire surfaces between the two layers. Alternatively, the adhesive can be applied in a pattern (e.g., grid) or random fashion whereby the adhesive does not substantially contact the entire surface area of the two layers, but rather forms a discontinuous intermediate layer between the two adhered surfaces. Each of the first, second, and base layers (or first, second, third, and fourth layers when present) of the absorbent pad of the present invention can be adhered together with continuous adhesive layers, or with discontinuous adhesive layers, or some of the adhesive layers can be continuous adhesive layers, and other adhesive layers can be discontinuous layers. Each of the adhesive layers can comprise the same adhesive material (as described herein), or one or more of the adhesive layers can comprise a different adhesive material (as described herein).

The present invention can be assembled from the component layers by any suitable method known in the art. In one embodiment of the invention, rolls of each layer are combined such that the first layer is disposed over the second, which is disposed over the base (or in some embodiments, third, which is disposed over the fourth), and the combined layers are then cut to the appropriate size and the edges adhered together. In another embodiment of the invention, sheets of a suitable size are cut from rolls of each individual layer, then combined in the appropriate order and the edges are adhered together. In yet another embodiment of the invention, the dimension of the base layer exceeds that of the second layer in either width, length or both by 1 inch to 5 inches. The second layer can be disposed over the base layer such that the base layer extends about 0.5 to about 2.5 inches beyond the second layer on either opposing sides or all sides, and the material of the base layer which extends beyond the second layer can be folded over and adhered to the second layer by any known means in the art. A first layer of the same dimensions as the second layer can be disposed over and adhered to the second layer.

In a further embodiment of the invention, the dimensions of the fourth layer and the third layer exceeds that of the second layer in either width, length or both by 1 inch to 5 inches. The third layer is disposed over the fourth layer, and the second layer can be disposed over the third such that the third and fourth layers extend about 0.5 to about 2.5 inches beyond the second layer on either opposing sides or all sides. The material of the third and fourth which extends beyond the second layer can be folded over and adhered to the second layer by any known means in the art. A first layer of the same dimensions as the second layer can be disposed over and adhered to the second layer.

The pads of the present invention can be of any suitable size. In one embodiment of the invention, the pads are about 36" by about 31". In one embodiment of the invention, the pads are about 36" by about 30". In yet another embodiment of the invention, the pads are about 36" by about 24". In certain embodiment, the pads are about 36" by about 23". In another embodiment the pads are about 30" by about 30". In yet another embodiment, the pads are about 24" by about 18". In a further embodiment, the pads are about 24" to about 17".

In a certain embodiment, the absorbent pad of the present invention has a Total Absorption Capacity, as measured by ISO Standard 11948-1, from about 4,000 g/m$^2$ to about 4,500 gm$^2$, for example about 4,000 g/m$^2$, about 4,100 g/m$^2$, about 4,200 g/m$^2$, about 4,300 g/m$^2$, about 4,400 g/m$^2$ or about 4,500 g/m$^2$.

The rate of acquisition and rewet properties of the pad of the present invention can be determined by any suitable method, for example the Medi-Cal method. The Medi-Cal acquisition rate and rewet test protocols comprise laying the pad of the present invention (as described herein) on a flat surface, then rapidly adding 100 or 200 mL of a 0.09% saline solution onto the center of the pad (the target area). The time required for the saline solution to pass through the top sheet of the pad is the rate of acquisition. Approximately 12 minutes after adding the saline solution to the pad, a preweighed (~10 g) stack of dry filter paper is placed on the center of the target area, and weighted with a 1.0 psi weight. After 1 minute, the filter paper stack is removed and weighed. The weight of moisture absorbed by the filter paper stack is the rewet value.

Suitable rewet values determined by the Medi-Cal method fall within the range of about 1 g to about 3 g, e.g., about 1 g, about 1.1 g, about 1.2 g, about 1.3 g, about 1.4 g, about 1.5 g, about 1.6 g, about 1.7 g, about 1.8 g, about 1.9 g, about 2.0 g, about 2.1 g, about 2.2 g, about 2.3 g, about 2.4 g, about 2.5 g, about 2.6 g, about 2.7 g, about 2.8 g, about 2.9 g, or about 3.0 g.

Suitable rate of acquisition values determined by the Medi-Cal method fall within the range of about 110 sec to about 180 sec, e.g., about 110 sec, about 115 sec, about 120 sec, about 125 sec, about 130 sec, about 135 sec, about 140 sec, about 145 sec, about 150 sec, about 155 sec, about 160 sec, about 165 sec, about 170 sec, about 175 sec or about 180 sec.

Figure 2:
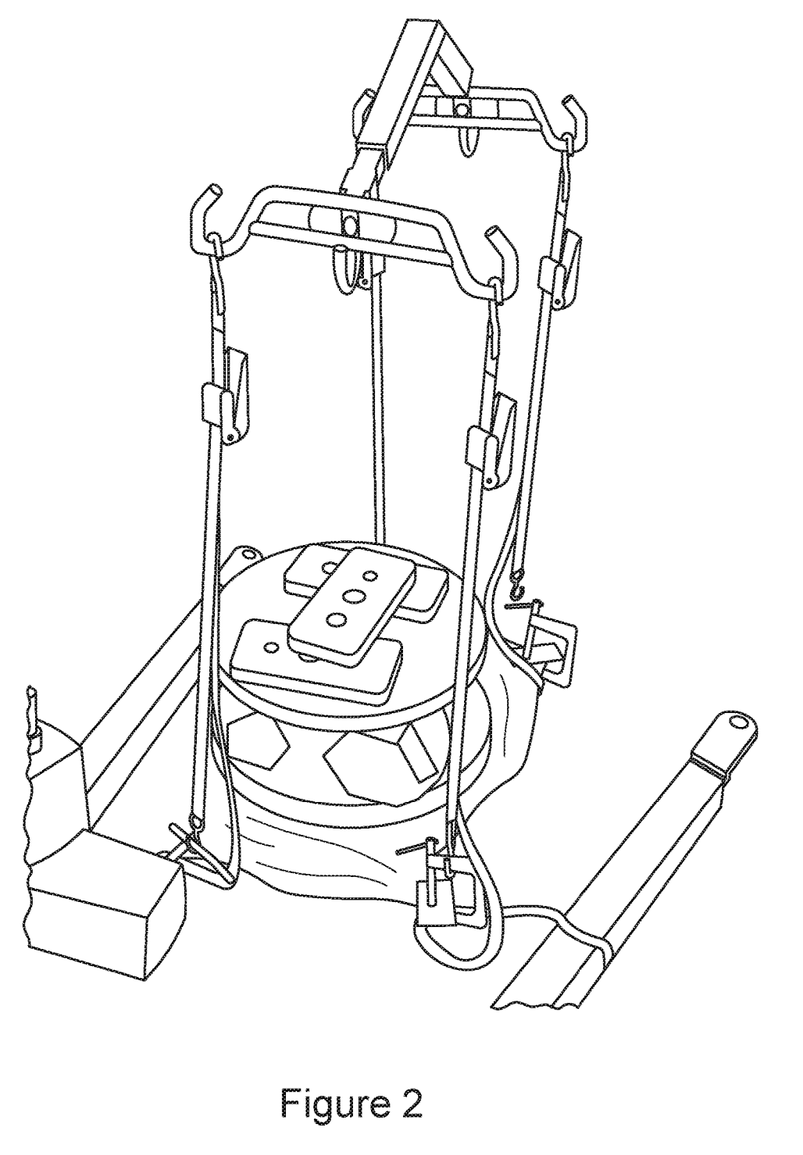
FIG. 2. Maximum Lift Weight testing device.

The "Max Lift Weight" is the maximum weight the pad can support while being lifted at two or more points without tearing. The Max Lift Weight can be tested by attaching clamps to at least two edges or corners of the pad and placing weights on the pad. The clamps can then be attached to a lifting device. (FIG. 2). In certain embodiments of the invention, the absorbent pad has a Max Lift Weight in the range of up to about 425 lbs to up to about 100 lbs. For Example, the absorbent pad of the present invention can have a Max Lift Weight of up to about 425 lbs, up to about 415 lbs, up to about 370 lbs, up to about 325 lbs, up to about 280 lbs, up to about 235 lbs, up to about 190 lbs, up to about 145 lbs, or up to about 100 lbs.

In a particular embodiment of the invention, the absorbent pad, after exposure to about 1 mL to about 500 mL of ASTM synthetic urine or a 1% saline solution has a Max Lift Weight in the range of up to about 415 lbs to up to about 100 lbs. For example, the absorbent pad of the present invention can have a Max Lift Weight after exposure to about 1 mL to about 1000 mL of ASTM synthetic urine or a 1% saline solution of up to about 325 lbs, of up to about 415 lbs, up to about 370 lbs, up to about 325 lbs, up to about 280 lbs, up to about 235 lbs, up to about 190 lbs, up to about 145 lbs, or up to about 100 lbs.

In some embodiments of the invention, the absorbent pad has tensile strength at break, when measured by the ASTM D 882 method, in the range of about 50 N/25 mm to about 90 N/25 mm in the machine direction. For example, the pad can have a tensile strength at break in the machine direction of about 50 N/25 mm, about 60 N/25 mm, about 70 N/25 mm, about 80 N/25 mm, or about 90 N/25 mm, inclusive of all ranges and subranges therebetween.

In other embodiments of the invention, the absorbent pad has tensile strength at break, when measured by the ASTM D 882 method, in the range of about 30 N/25 mm to about 60 N/25 mm in the cross direction. For example, the pad can have a tensile strength at break in the cross direction of about 30 N/25 mm, about 35 N/25 mm, about 40 N/25 mm, about 45 N/25 mm, about 50 N/25 mm, about 55 N/25 mm, or about 60 N/25 mm, inclusive of all ranges and subranges therebetween.

In another embodiment of the invention, the elongation at break of the absorbent pad, when tested by the ASTM D 882 method, is in the range of about 35% to about 115% in the machine direction. For example, the pad can have an elongation at break in the machine direction of about 35%, about 55%, about 45%, about 65%, about 75%, about 85%, about 95%, about 105% or about 115%, inclusive of all ranges and subranges therebetween.

In a particular embodiment of the invention, the elongation at break of the absorbent, when tested by the ASTM D 882 method, is in the range of about 45% to about 105% in the cross direction. For example, the pad can have an elongation at break in the cross direction of about 45%, about 55%, about 65%, about 75%, about 85%, about 95%, or about 105%, inclusive of all ranges and subranges therebetween.

In particular embodiments of the invention, the absorbent pad has a tensile strength at 25% elongation, when measured by the ASTM D 882 method, in the range of about 35 N/25 mm to about 55 N/25 mm in the machine direction. For example, the absorbent pad can have a tensile strength at 25% elongation in the machine direction of about 35 N/25 mm, about 40 N/25 mm, about 45 N/25 mm, about 50 N/25 mm, or about 55 N/25 mm, inclusive of all ranges and subranges therebetween.

In a particular embodiment of the invention, the absorbent pad has tensile strength at 25% elongation, when measured by the ASTM D 882 method, in the range of about 20 N/25 mm to about 40 N/25 mm in the cross direction. For example, the absorbent pad can have a tensile strength at break in the cross direction of about 20 N/25 mm, about 25

N/25 mm, about 30 N/25 mm, about 35 N/25 mm, or about 40 N/25 mm, inclusive of all ranges and subranges therebetween.

In a particular embodiment of the invention, a single absorbent pad of the present invention is placed under an incontinent individual, and the single absorbent pad absorbs fluids, protects skin dryness and/or protects the bedding from fluids. Protecting skin dryness means the individual's skin which is in contact with the pad remains reasonably dry after the pad has been exposed to urine or other fluids. Protecting the bedding means that less than 10% of the urine or other fluid which is expelled onto the pad makes contact with the bedding underneath the pad. In yet another embodiment of the invention, at least one caregiver can lift or reposition the patient by lifting the single absorbent pad of the present invention, disposed beneath the patient, at two or more edges or corners.

EXAMPLES

Example 1

A. Absorbent Pad

The first layer is a spunbond, nonwoven with a weight of 16.96 gsm (PGI). The second layer is a thermobonded absorbent airlaid core made from 103 gsm macerated wood pulp and 25 gsm of super absorbent polymer (Super Core® McAirlaids). The third layer is an air permeable PE film with a weight of 35 gsm and a MVTR of 3,600 $g/m^2/day$ (PGI). The fourth layer is a 50 gsm spunbond nonwoven back sheet (PGI). The top layer and the edges where the layers meet are glued together using hot melt adhesive.

B. Strength Testing

The strength of the pad from Example 1A was tested with ASTM E 252 to measure the basis weight and ASTM D 882 to measure tensile strength and elongation at break. The results are shown in Table 1:

| Property | Weight/Strength |
| --- | --- |
| Basis Weight | 71.5 ± 6 $g/m^2$ |
| Tensile Strength at break in the Machine Direction | 70 ± 16 N/25 mm |
| Tensile Strength at break in the Cross Direction | 45 ± 10 N/25 mm |
| Elongation at Break in the Machine Direction | 75 ± 40% |
| Elongation at Break in the Cross Direction | 75 ± 30% |
| Tensile Strength at 25% Elongation in the Machine Direction | 47 ± 8 N/25 mm |
| Tensile Strength 25% Elongation in the Cross Direction | 28 ± 8 N/25 mm |

C. Max Lift Weight Testing

The Max Lift Weight was tested by placing the pad flat on the ground with the first layer up, loading weights on top of the pad and centering the weights. The corners of the pad were clamped into the lifting device as shown in FIG. 2. The absorbent pad and weights were lifted 2-3 inches above the ground for two minutes, while observing any tearing or other failures to the structural integrity of the pad. The testing was repeated until failure. The absorbent pad of Example 1A was held for two minutes with 415 lbs with no observed tearing or ripping.

The wet Max Lift Weight was tested in a similar manner after applying 500 cc of liquid to the absorbent pad. The absorbent pad of Example 1A was held for two minutes with 425 lbs with no observed tearing or ripping.

We claim:

1. An absorbent pad comprising:
   a) an absorbent layer, comprising at least one super absorbent material;
   b) a base layer disposed adjacent to the absorbent layer, comprising an air-permeable material,
   wherein the tensile strength of the base layer at break, when measured by the ASTM D 882 method, is in the range of about 45 to 100 N/25 mm in the machine direction and about 30 to 60 N/25 mm in the cross direction, wherein the base layer comprises two layers:
   c) a first base layer disposed under the absorbent layer, comprising a hydrophobic, breathable film; and
   d) a second base layer disposed under the first base layer, comprising an air-permeable material.

2. The absorbent pad of claim 1, wherein the absorbent layer comprises formed or unformed material.

3. The absorbent pad of claim 2, wherein the absorbent layer comprises a formed material, and the formed material is an air-laid material.

4. The absorbent pad of claim 3, wherein the air-laid material comprises a natural fiber.

5. The absorbent pad of claim 4, wherein the natural fiber is cellulose.

6. The absorbent pad of claim 5, wherein the cellulose is selected from one or more of the group consisting of wood fibers, plant fibers, field crop fibers, and fluff pulp.

7. The absorbent pad of claim 3, wherein the air-laid material is thermobonded.

8. The absorbent pad of claim 1, wherein the absorbent layer comprises natural or synthetic material.

9. The absorbent pad of claim 1, wherein the absorbent layer comprises a super absorbent polymer.

10. The absorbent pad of claim 9, wherein the super absorbent polymer comprises a polymer or copolymer of sodium polyacrylate.

11. The absorbent pad of claim 9, wherein the absorbent layer further comprises about 90-110 gsm of macerated wood pulp.

12. The absorbent pad of claim 9, wherein the absorbent layer comprises about 20-30 gsm of super absorbent polymer.

13. The absorbent pad of claim 1, wherein the absorbent layer has moisture absorption capacity in the range of about 50 $cc/m^2$ to about 20,000 $cc/m^2$ as measured by the ISO11948-1 test method.

14. The absorbent pad of claim 1, wherein the super absorbent material does not substantially swell or separate from the base layer when wet.

15. The absorbent pad of claim 1, wherein the first base layer comprises a polyethylene film.

16. The absorbent pad of claim 15, wherein the polyethylene film is perforated.

17. The absorbent pad of claim 1, wherein the first base layer has a weight in the range of about 20 gsm to about 45 gsm.

18. The absorbent pad of claim 1, wherein the first base layer has a moisture vapor transmission rate in the range of about 1,000 $g/m^2/day$ to about 10,000 $g/m^2/day$.

19. The absorbent pad of claim 1, wherein the second base layer comprises a nonwoven material.

20. The absorbent pad of claim 19, wherein the nonwoven material is selected from the group consisting of a hydrophobic nonwoven material, a staple nonwoven material, a melt blown nonwoven material, a spunmelt nonwoven material, a spunbond, nonwoven material, SMS (spunbond meltblown spunbond) materials, spun lace materials, needlefelted materials, a thermal bonded nonwoven, a trough air bonded nonwoven material, a spunlaid nonwoven material, or a combination thereof.

21. The absorbent pad of claim 20, wherein the nonwoven material comprises a polymer selected from the group consisting of polypropylene, polyethylene, polyethylene terephthalate, polyamide, viscose rayon, nylon, at least one biodegradable polymeric material and combinations thereof.

22. The absorbent pad of claim 1, wherein the second base layer has a weight in the range of about 30 to about 90 gsm.

23. The absorbent pad of claim 1, wherein the absorbent layer, and first and second base layers are adhered together.

24. The absorbent pad of claim 23, wherein the layers are adhered together using an adhesive.

25. The absorbent pad of claim 24, wherein the adhesive is a hot melt adhesive.

26. The absorbent pad of claim 1, wherein the pad has rewet of about 1 g to about 3 g.

27. The absorbent pad of claim 1, wherein
the absorbent layer comprises a thermobonded absorbent airlaid core comprising cellulose fibers and super absorbent polymers;
the first base layer is a perforated polyethylene film;
and the second base layer is a nonwoven sheet with a weight of about 15 gsm to about 90 gsm.

28. The absorbent pad of claim 1, wherein
the absorbent layer has an absorption capacity in the range of about 50 $cc/m^2$ to about 20,000 $cc/m^2$ as measured by the ISO11948-1 test;
the first base layer has a weight of about 20 to about 45 gsm and a Moisture Vapor Transmission Rate in the range of about 1,000 $g/m^2$/day to about 10,000 $g/m^2$/day; and
the second base layer has a weight of about 30 gsm to about 90 gsm.

29. The absorbent pad of claim 1, wherein the pad has a lift weight of at least 400 lbs.

30. The absorbent pad of claim 1, wherein the pad has a maximum lift weight up to about 325 lbs.

31. The absorbent pad of claim 1, wherein the pad has a maximum lift weight of up to at least 425 lbs.

32. The absorbent pad of claim 1, wherein after exposure to about 1 to about 1000 ccs of fluid, the pad has a max lift weight of up to 325 lbs.

33. The absorbent pad of claim 1, wherein the tensile strength at break, when measured by the ASTM D 882 method, is about 70±16 N/25 mm in the machine direction and about 45±10 N/25 mm in the cross direction.

34. The absorbent pad of claim 1, wherein the elongation at break, when tested by the ASTM D 882 method, is about 75±40% in the machine direction and about 75±30% in the cross direction.

35. The absorbent pad of claim 1, wherein the tensile strength at 25% elongation, when measured by the ASTM D 882 method, is about 47±8 N/25 mm in the machine direction and about 28±8 N/25 mm in the cross direction.

36. The absorbent pad of claim 1, further comprising a means for lifting and/or repositioning a patient on the pad.

37. The absorbent pad of claim 1, further comprising handles.

38. A method of absorbing fluids, protecting bedding, and/or maintaining skin dryness of an incontinent patient, comprising placing the absorbent pad of claim 1 under the patient, whereby the absorbent pad absorbs fluids, and/or protects bedding, and/or maintains skin dryness.

39. The method of claim 38, further comprising lifting or repositioning the patient with the absorbent pad.

* * * * *